United States Patent

Broekhof et al.

[11] Patent Number: 4,643,844
[45] Date of Patent: Feb. 17, 1987

[54] PERFUME COMPOSITIONS AND PERFUMED ARTICLES CONTAINING DIHYDRO- AND/OR TETRAHYDRO-NAPHTHOLS AS FRAGRANCE MATERIAL

[75] Inventors: Nicolaas L. J. M. Broekhof, Naarden; Antonius J. A. van der Weerdt, Huizen; Jogchum Hofma, Amersfoort, all of Netherlands

[73] Assignee: 501 Naarden International N.V., Naarden-Bussum, Netherlands

[21] Appl. No.: 705,620

[22] Filed: Feb. 26, 1985

[30] Foreign Application Priority Data

Feb. 29, 1984 [NL] Netherlands ............ 8400657

[51] Int. Cl.$^4$ ............ A61K 7/46; C11B 9/00
[52] U.S. Cl. ............ 252/522 R; 568/734; 568/743
[58] Field of Search ............ 252/522 R; 568/734, 568/743

[56] References Cited

U.S. PATENT DOCUMENTS 3,629,337 12/1971 Degginger et al. ............ 568/734
3,726,911 4/1973 Degginger ............ 568/734

OTHER PUBLICATIONS

Viktorova et al., Chemical Abstracts, vol. 57, p. 1119i.
Degginger, Chemical Abstracts, vol. 76(1972), p. 126667k.
Degginger et al., Chemical Abstracts, vol. 77(1972), p. 88126.
Degginger et al., Chemical Abstracts, vol. 78(1973), p. 159326t.

Primary Examiner—Werren B. Lone
Attorney, Agent, or Firm—Brumbaugh, Graves, Donohue & Raymond

[57] ABSTRACT

Perfume compositions and perfumed articles containing dihydro- and/or tetrahydro-1-naphthol derivatives of the formula

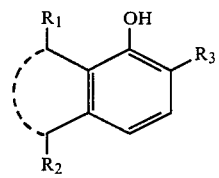

wherein the dotted lines represent carbon-carbon single or double bonds with the proviso that no more than one of them is a double bond and wherein $R_1$, $R_2$ and $R_3$ independently are methyl groups or hydrogen atoms; said naphthol derivatives have a very natural leather-like odor.

11 Claims, No Drawings

PERFUME COMPOSITIONS AND PERFUMED ARTICLES CONTAINING DIHYDRO- AND/OR TETRAHYDRO-NAPHTHOLS AS FRAGRANCE MATERIAL

The invention relates to perfume compositions containing dihydronaphthol derivatives and/or tetrahydronaphthol derivatives as fragrance material, and to articles perfumed with these compounds or with perfume compositions containing these compounds respectively.

There is a continuing interest in the preparation and application of synthetic fragrance materials, because contrary to materials of natural origin, synthetics can always be prepared in the quantity desired and with uniform quality.

In particular there is a demand for synthetic fragrance materials having a natural odour character.

Leather has a characteristic, very complex, but highly esteemed odour. Hitherto, the leather odour could only be approached with combinations of many raw materials, known as such in the fragrance industry. Traditionally important components of leather odour compositions are birchtar oil and substituted phenols and phenol ethers, such as p-tert-butylphenol, p-tert-butyl-meta-cresol and its methylether. (S. Arctander, Perfume and Flavor Chemicals, Monograph numbers 504, 429 and 430.) However, a really satisfactory leather odour could not be obtained with the components thus far known.

It was found that dihydro- and tetrahydro-1-naphthol derivatives of the formula

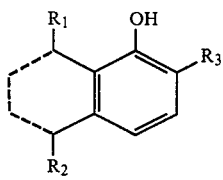

wherein the dotted lines represent carbon-carbon single or double bonds with the proviso that not more than one of them is a double bond and wherein $R_1$, $R_2$ and $R_3$ independently are methyl groups or hydrogen atoms, are strong and stable fragrance materials with a leather-like odour. Especially preferred are those compounds wherein either both $R_1$ and $R_2$ are methyl groups or only $R_3$ is a methyl group, or wherein all are hydrogen atoms.

The compounds of the invention are very suitable to be used as such or in combination with components which are usual for that purpose, to give a delicate and very natural leather-like odour to all kinds of articles and materials. The compounds may also be used advantageously to give a leathery aspect to perfume compositions.

Most of the compounds of the present invention are known as such in the chemical literature, yet they were unknown to the fragrance industry. Tetrahydro-1-naphthol ethyl ether is described in Arctander (No. 2921) as having a sweet, warm floral and weakly woody odour, which does not in any way resemble the odour of the compounds of the present invention. Moreover, Arctander reports this ether as never having aroused any interest in the fragrance industry.

The published German patent application No. 3215341 reported tetrahydro-1-naphthol as being useful for preventing dandruff. The compound is described as having an agreeable medicinal odour which is said to make additional perfuming of shampoos and hairlotions containing this compound unnecessary. However a medicinal odour, although appropriate for products having a certain medicinal action like anti-dandruff shampoos, is not really appreciated by many people, and thus this description does not suggest the compound to be generally useful in perfumery. More specifically it does not suggest usefulness for giving a delicate leather-like odour.

The compounds of the present invention may be prepared according to methods generally known in the art. Such methods have been described e.g. in Organic Synthesis, Coll. Volume IV, pages 887–9; J. Org. Chem., Vol. 36 (1971) pages 3345–3349; J. Am. Chem. Soc., Vol. 61 (1939) pages 765–767; published German patent application No. 2333847 and references cited in these publications.

The phrase "perfume composition" is used to mean a mixture of fragrance materials and optionally auxiliary substances, which may be dissolved in an appropriate solvent or mixed with a powdery substrate and used to impart a desired odour to the skin and/or to various products. Examples of said products are soaps, detergents, air fresheners, room sprays, pommanders, candles, cosmetics such as creams, ointments, colognes, pre- and after-shave lotions, talcum powders, body deodorants and antiperspirants. The compounds according to the invention are also especially suitable to impart a leather odour to all kinds of products, in particular leather substitutes.

Fragrance materials and mixtures thereof which can be used in combination with the compounds of the present invention for the preparation of perfume compositions include natural products such as essential oils, absolutes, resinoids, resins, concretes etc., but also synthetic fragrance materials such as hydrocarbons, alcohols, aldehydes, ketones, ethers, acids, esters, acetals, ketals, nitriles etc., being saturated or unsaturated, and aliphatic, carbocyclic or heterocyclic compounds.

Fragrance materials to be used in combination with the compounds according to the invention include geraniol, geranyl acetate, linalool, linalyl acetate, tetrahydro-linalool, citronellol, citronellyl acetate, dihydro-myrcenol, dihydro-myrcenyl acetate, tetrahydro-myrcenol, terpineol, terpinyl acetate, nopol, nopyl acetate, β-phenyl-ethanol, β-phenyl-ethyl acetate, benzyl alcohol, benzyl acetate, benzyl salicylate, benzyl benzoate, amyl salicylate, styrallyl acetate, dimethyl-benzyl carbinol, trichloromethyl-phenylcarbinyl acetate, p-tert-butyl-cyclohexyl acetate, isononyl acetate, vetiveryl acetate, vetiverol, α-hexyl-cinnamaldehyde, 2-methyl-3(p-tert-butylphenyl)-propanal, 2-methyl-3(p-isopropylphenyl-propanal, 3-(p-tert-butylphenyl)-propanal, tricyclodecenyl acetate, tricyclodecenyl propionate, 4-(4-hydroxy-4-methylpentyl)-cyclohex-3-ene carbaldehyde, 4-acetoxy-3-pentyl-tetrahydropyran, 3-carboxymethyl-2-pentyl-cyclopentane, 2-n-heptyl-cyclopentanone, 3-methyl-2-pentylcyclopentan-2-one, n-decenal, n-dodecenal, dec-9-enol, phenoxy-ethyl isobutyrate, phenyl-acetaldehyde dimethylacetal, phenyl-acetaldehyde diethylacetal, geranyl nitrile, citronellyl nitrile, cedryl acetate, 3-iso-camphyl-cyclohexanol, cedryl methyl ether, isolongifolanone, aubepine nitrile, aubepine, heliotropine, coumarin, eugenol, vanillin, diphenyl oxide, hydroxy-citronellal, ionones, methyl-ionones, iso-methyl-ionones, irones, cis-hex-3-enol and esters thereof, indan musks, tetralin musks, isochroman musks, macrocyclic ketones, macrolactone musks, ethylene brassylate, aromatic nitromusks.

Auxiliary agents and solvents that may be incorporated into perfume compositions containing the compounds according to the invention are e.g. ethanol, isopropanol, diethylene glycol monoethylether, diethyl phthalate, etc..

The amounts of the compounds of the present invention which can be used in perfume compositions or in products to be perfumed, may vary within broad limits and depend e.g. on the kind of products wherein the compounds are used, the nature and the amount of other components in the composition and the desired odour effect. Thus, it is only possible to give rough limits, which however present a person skilled in the art with sufficient information to enable him to use the compounds for his own purpose. In most cases only 0.1% by weight in a perfume composition will produce a clearly perceptible odour effect. On the other hand, for a specific leather odour up to 90% or even more may be used in a composition. In products perfumed with perfume compositions according to the invention the concentration depend on the amount of composition used in the product and thus is proportionally lower.

The following examples only illustrate the preparation and the use of the compounds according to the invention and do not restrict the invention thereto.

EXAMPLE I 5,8-Dihydro-1-naphthol was prepared as described in Organic Synthesis, Coll. Vol. IV, pages 887–9.

The compound has a soft, animalic and agreeable leather-like odour.

5,8-Dihydro-1-naphthol was isomerised to a mixture of 1 part 7,8-dihydro-1-naphthol and 2 parts 5,6-dihydro-1-naphthol by heating for 10 hours at 95° C. with a solution of 1.1 moleq of tert-BuOK in DMSO. The mixture has an agreeable odour very much resembling that of 5,8-dihydro-1-naphthol.

5,8-Dihydro-1-naphthol was hydrogenated as described in Organic Synthesis, Coll. Vol. IV, pages 887–9 to yield tetrahydro-1-naphthol. The compound has a very strong and very distinct leather odour.

5,8-Dimethyl-tetrahydro-1-naphthol was prepared as described in J. Org. Chem., Vol. 36 (1971) pages 3345–3349. The compound has a distinct leather-like odour with a slight camphoraceous nuance.

EXAMPLE II

2-Methyl-tetrahydro-1-naphthol was prepared as follows:

130 g (0.88 mol) tetrahydro-1-naphthol was dissolved in 100 ml ethanol. 70.5 g (0.96 mol) diethylamine was added as a 25% solution in water, at 10°–15° C.

Thereafter 74.5 g (0.95 mol) 35% formalin was added slowly, keeping the temperature of the mixture at 10°–15° C. Stirring was continued for 4 hours, while the temperature was raised to 65° C.

After cooling to room temperature, the layers were separated and the aqueous layer was extracted twice with toluene. The combined organic layers were washed with water and dried over $MgSO_4$.

The residue obtained after evaporation of the solvent was distilled to yield 89% of 2-diethylamino-tetrahydro-1-naphthol.

43.5 g of this product was dissolved in 100 ml ethanol and 4.8 g of 5% Pd/C catalyst and 2.4 g of p-toluenesulfonic acid were added.

The mixture was hydrogenated during 4 hours at 45° C. under a hydrogen-pressure of 300 kPa. Subsequently the catalyst was removed by filtration and the solvent was evaporated. The residue was dissolved in 100 ml of water and extracted with ether. The waterlayer was acidified with hydrochloric acid and once more extracted with ether. The combined organic layers were washed with dilute hydrochloric acid, dried over $MgSO_4$ and evaporated. The residu was distilled to afford the desired 2-methyl-tetrahydro-1-naphthol in 69% yield.

The compound has a strong leather-like odour with an animalic and slightly camphoraceous nuance.

EXAMPLE III

A perfume composition for a "Men's cologne" was prepared according to the following recipe:

| | |
|---|---|
| Acetylcedrene | 200 parts by weight |
| Bergamot oil | 190 parts by weight |
| Lemon oil | 90 parts by weight |
| α-Hexyl-cinnamaldehyde | 90 parts by weight |
| Lavandin oil | 60 parts by weight |
| Patchouli oil | 50 parts by weight |
| Methyl dihydrojasmonate | 50 parts by weight |
| 5-Acetyl-3-isopropyl-1,1,2,6-tetra-methyl-indan | 30 parts by weight |
| Muguet synthetic | 30 parts by weight |
| Isolongifolanone | 30 parts by weight |
| Aspic oil | 30 parts by weight |
| Musk ketone | 20 parts by weight |
| Labdanum resinoid | 20 parts by weight |
| Ylang oil | 20 parts by weight |
| Menthol | 10 parts by weight |
| Mousse de chene absolute | 10 parts by weight |
| Isobutylquinolin* | 10 parts by weight |
| Galbanum oil | 10 parts by weight |
| Styrallyl acetate | 5 parts by weight |
| Clove bud oil | 5 parts by weight |
| Undecylenic aldehyde* | 5 parts by weight |
| Methyl-nonyl-acetaldehyde* | 5 parts by weight |
| Tetrahydro-1-naphthol | 30 parts by weight |
| | 1000 parts by weight |

*10% by weight dissolved in diethylene glycol monoethylether.

Comparable compositions were prepared substituting 60 parts by weight of 5,8-dihydro-1-naphthol or the mixture of 7,8- and 5,6-dihydro-1-naphthol prepared according to Example I, for 30 parts tetrahydro-1-naphthol in the above mentioned recipe.

EXAMPLE IV

A perfume composition for an after shave lotion was prepared according to the following recipe:

| | |
|---|---|
| Cedryl acetate | 230 parts by weight |
| Patchouli oil | 100 parts by weight |
| Lemon oil | 90 parts by weight |
| Lavender oil | 90 parts by weight |
| Benzyl salicylate | 90 parts by weight |
| Musk ketone | 53 parts by weight |
| Bergamot oil | 50 parts by weight |
| Rose synthetic | 50 parts by weight |
| Coumarin | 30 parts by weight |
| Jasmin synthetic | 30 parts by weight |
| Methyl dihydrojasmonate | 30 parts by weight |
| Amber synthetic | 25 parts by weight |
| Galbanum resinoid | 20 parts by weight |
| Sandalwood oil East Indian | 20 parts by weight |
| Geranium oil Bourbon | 20 parts by weight |
| Mousse de chene absolute | 10 parts by weight |

| | |
|---|---|
| Basil oil | 10 parts by weight |
| Origanum oil | 2 parts by weight |
| Tetrahydro-1-naphthol | 50 parts by weight |
| | 1000 parts by weight |

Comparable compositions were prepared substituting 80 parts by weight of 2-methyl-tetrahydro-1-naphthol or 5,8-dimethyl-tetrahydro-1-naphthol prepared according to Examples II and I respectively, for 50 parts of tetrahydro-1-naphthol in the above mentioned recipe.

EXAMPLE V

An after shave lotion, perfumed with a composition according to Example IV, was prepared according to the following recipe:

| | |
|---|---|
| A. | 0.3 parts by weight of l-menthol |
| | 0.5 parts by weight of Uvinol D 50[1] |
| | 30.0 parts by weight of propylene glycol |
| | 535.0 parts by weight of ethanol |
| B. | 2.0 parts by weight of aluminium chloro hydrate allantoinate |
| | 2.0 parts by weight of lactic acid |
| | 400.0 parts by weight of water (demineralised) |
| C. | 20 parts by weight of perfume (Example IV) |
| | 10 parts by weight of Cremophor RH40[2] |

[1]Trademark of BASF for 2,2',4,4'-tetrahydroxy-benzophenone.
[2]Trademark of BASF for a reaction product of hydrogenated castor oil and ethylene oxide.

The components listed under A, B and C were separately mixed, to obtain the mixtures A, B and C.

Mixture B was added to a mixture A while stirring well. Thereafter mixture C was added and the lot was stirred to obtain a homogeneous mixture. Thus a somewhat astringent after shave lotion was obtained having an odour characterized by an agreeable leather note.

We claim:

1. A perfume composition comprising a mixture of fragrance materials comprising an effective odorant amount of one or more dihydro- or tetrahydro-1-naphthol derivatives having a structure according to the formula

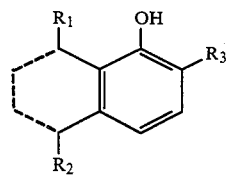

(I)

wherein the dotted lines represent carbon-carbon single or double bonds, with the proviso that not more than one of them is a double bond, and wherein $R_1$, $R_2$ and $R_3$ independently are methyl groups or hydrogen atoms together with other fragrance materials.

2. A perfume composition according to claim 1, comprising at least one dihydro- or tetrahydro-1-naphthol derivative of the formula I wherein $R_1$ and $R_2$ are both methyl groups and $R_3$ is a methyl group or a hydrogen atoms.

3. A perfume composition according to claim 1, comprising at least one dihydro- or tetrahydro-1-naphthol derivative of the formula I, wherein $R_1$ and $R_2$ are both hydrogen and $R_3$ is a methyl group.

4. A perfume composition according to claim 1, comprising at least one dihydro- or tetrahydro-1-naphthol derivative of the formula I wherein $R_1$, $R_2$ and $R_3$ are hydrogen atoms.

5. A perfume composition according to claim 1, comprising at least 0.1% by weight of a dihydro- or tetrahydro-1-naphthol derivative of the formula I defined in said claim 1.

6. A perfumed product comprising an effective odorant amount of one or more dihydro- or tetrahydro-1-naphthol derivatives having a structure according to the formula

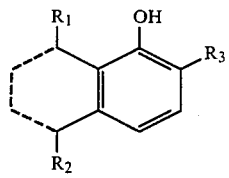

wherein the dotted lines represent carbon-carbon single or double bonds, with the proviso that not more than one of them is a double bond, and wherein $R_1$, $R_2$ and $R_3$ independently are methyl groups or hydrogen atoms.

7. A perfumed product according to claim 6, wherein $R_1$ and $R_2$ are both methyl groups, and $R_3$ is a methyl group or a hydrogen atom.

8. A perfumed product according to claim 6, wherein $R_1$ and $R_2$ are both hydrogen, and $R_3$ is a methyl group.

9. A perfumed product according to claim 6, wherein $R_1$, $R_2$ and $R_3$ are hydrogen atoms.

10. A perfumed product according to claim 6, comprising at least 0.1% by weight of a dihydro- or tetrahydro-1-naphthol derivative.

11. A method of imparting a leathery note to perfume composition comprising adding to the perfume composition an effective odorant amount of at least one dihydro- or tetrahydro-1-naphthol derivative of the formula

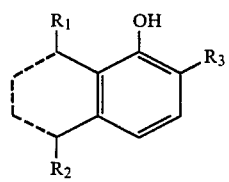

wherein the dotted lines represent carbon-carbon sinle or double bonds, with the proviso that not more than one of them is a double bond, and wherein $R_1$, $R_2$ and $R_3$ independnetly are methyl groups or hydrogen atoms.

* * * * *